United States Patent
Hayashi

(10) Patent No.: US 6,658,288 B1
(45) Date of Patent: Dec. 2, 2003

(54) APPARATUS AND METHOD FOR AIDING THROMBOSIS THROUGH THE APPLICATION OF ELECTRIC POTENTIAL

(75) Inventor: Reid Hayashi, Palo Alto, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/565,245

(22) Filed: May 5, 2000

(51) Int. Cl.⁷ .................................................. A61N 1/30
(52) U.S. Cl. ...................................................... 604/20
(58) Field of Search .......................... 623/1, 1.1, 1.35, 623/1.13, 11, 1.4; 604/20, 19; 606/25, 57, 104

(56) References Cited

U.S. PATENT DOCUMENTS

| | | |
|---|---|---|
| 3,908,662 A | 9/1975 | Razgulov et al. |
| 4,148,664 A | 4/1979 | Cruz, Jr. |
| 4,214,587 A | 7/1980 | Sakura, Jr. |
| 4,394,373 A | 7/1983 | Malette et al. |
| 4,631,188 A | 12/1986 | Stoy et al. |
| 4,640,279 A | 2/1987 | Beard |
| 4,693,249 A | 9/1987 | Schenck et al. |
| 4,882,466 A * | 11/1989 | Friel ............................ 219/219 |
| 4,919,744 A * | 4/1990 | Newman ....................... 156/292 |
| 5,108,407 A * | 4/1992 | Geremia et al. ............... 604/57 |
| 5,122,135 A | 6/1992 | Dürr et al. |
| 5,156,620 A * | 10/1992 | Pigott ........................... 604/916 |
| 5,192,310 A * | 3/1993 | Herweck et al. ............. 623/1.27 |
| 5,221,259 A | 6/1993 | Weldon et al. |
| 5,224,491 A * | 7/1993 | Mehra ........................... 607/126 |
| 5,262,974 A | 11/1993 | Hausman et al. |
| 5,330,528 A | 7/1994 | Lazim |
| 5,415,657 A | 5/1995 | Taymor-Luria |
| 5,522,836 A * | 6/1996 | Palermo ........................ 606/108 |
| 5,540,715 A | 7/1996 | Katsaros et al. |
| 5,562,641 A * | 10/1996 | Flomenblit et al. ........... 604/104 |
| 5,582,619 A | 12/1996 | Ken |
| 5,591,204 A | 1/1997 | Janzen et al. |
| 5,607,478 A | 3/1997 | Lentz et al. |
| 5,617,878 A | 4/1997 | Taheri |
| 5,624,449 A | 4/1997 | Pham et al. |
| 5,624,669 A | 4/1997 | Leung et al. |
| 5,649,949 A | 7/1997 | Wallace et al. |

(List continued on next page.)

FOREIGN PATENT DOCUMENTS

| | | |
|---|---|---|
| EP | 0747014 A1 | 12/1996 |
| WO | WO 97/03717 | 2/1997 |
| WO | WO 98/41167 | 9/1998 |

OTHER PUBLICATIONS

Guido Guglielmi, "Embolization of Intracranial Aneurysms with Detachable Coils and Electrothrombosis", Interventional Neuroradiology: Endovascular Therapy of the Central Nervous System, 1992, pp. 63–75.

Philip N. Sawyer and James W. Pate, "Bio–Electric Phenomena as an Etiologic Factor in Intravascular Thrombosis", Naval Medical Research Institute, vol. 175, pp. 103–107.

*Primary Examiner*—Daniel Robinson
(74) *Attorney, Agent, or Firm*—Fulwider Patton Lee & Utecht, LLP

(57) ABSTRACT

Disclosed are apparatus and methods for aiding thrombosis through the application of electric potential. In one embodiment, a hollow prosthesis is placed within a patient at a treatment site, such as at an aneurysm. The outer surface of a prosthesis is given a positive charge. The positive charge on the outer surface attracts negatively charged components of blood, thus facilitating the repair of perigraft flow. In another embodiment, a conductive wire is used to pierce a graft and enter an aneurysm sac. The wire is positively electrically charged to aid in thrombosis, thus facilitating the repair of perigraft flow.

7 Claims, 8 Drawing Sheets

U.S. PATENT DOCUMENTS

| | | |
|---|---|---|
| 5,653,370 A | 8/1997 | Bereiter et al. |
| 5,653,730 A | 8/1997 | Hammerslag |
| 5,665,117 A | 9/1997 | Rhodes |
| 5,667,767 A | 9/1997 | Greff et al. |
| 5,676,689 A | 10/1997 | Kensey et al. |
| 5,690,671 A | 11/1997 | McGurk et al. |
| 5,728,068 A * | 3/1998 | Leone et al. ............ 604/101.01 |
| 5,769,882 A | 6/1998 | Fogarty et al. |
| 5,785,679 A | 7/1998 | Abolfathi et al. |
| 5,795,318 A * | 8/1998 | Wang et al. .................... 604/8 |
| 5,860,948 A | 1/1999 | Buscemi |
| 5,871,537 A | 2/1999 | Holman et al. |
| 5,916,235 A | 6/1999 | Guglielmi |
| 5,925,683 A | 7/1999 | Park |
| 5,935,148 A | 8/1999 | Villar et al. |
| 5,941,888 A | 8/1999 | Wallace et al. |
| 5,951,599 A | 9/1999 | McCrory |
| 6,071,286 A * | 6/2000 | Mawad .................... 604/96.01 |
| 6,206,914 B1 * | 3/2001 | Soykan et al. ........... 604/891.1 |
| 6,358,276 B1 * | 3/2002 | Edwin ........................ 604/500 |

\* cited by examiner

APPARATUS AND METHOD FOR AIDING THROMBOSIS THROUGH THE APPLICATION OF ELECTRIC POTENTIAL

BACKGROUND OF THE INVENTION

The present invention is in the general field of surgical instruments. More specifically, the present invention relates to repairing leaking grafts or leaks around endovascular grafts. These devices are useful for treating a patient including preventing the rupture of an aneurysm that has been fitted with a graft that has perigraft flow.

Grafts are generally tubular-shaped or Y-shaped devices that may function to bridge an aneurysm sac and thus prevent blood from flowing through the sac. Clinical studies have shown that some graft implants suffer from perigraft flow (i.e., leaks around the outside of a graft). Such perigraft flow often does not improve over time. If blood were to leak and flow through the sac, thus pressurizing the sac, then the sac might rupture and thus threaten the life of the patient. Consequently, it is useful to employ a device to stop any leaking.

Sometimes, after the flow has been directed through the inserted graft, the pressure in the aneurysm sac may remain high because of collateral flow from other vessels into and out of the sac. These collateral flows often clot and cease by themselves or with the aid of other vascular techniques. However, this clotting does not always result in a reduction in pressure in the aneurysm sac. Therefore, it would be desirable to reduce this pressure within the aneurysm sac.

When describing parts of a catheter, use of the terms proximal and distal is with respect to a user, thus the tip of the catheter is most distal and an injection port is proximal. When describing parts of the graft, use of the terms inferior and superior is with respect to the patient, superior is toward the direction of the head and inferior is toward the direction of the feet. References to thrombosis herein shall include thrombosis, hemostasis, embolization, anastomotic sealing, and void filling.

What has been needed and heretofore unavailable is a relatively simplified, safe, fast-acting, and inexpensive invention for aiding thrombosis. The present invention satisfies these needs.

SUMMARY OF THE INVENTION

Briefly, and in general terms, the present invention is directed to an apparatus and method for aiding processes including thrombosis at a treatment site of a patient. Various apparatus and methods are provided that utilize the application of electric potential in order to repair, for example, perigraft flow.

In one aspect of the invention, there is provided an apparatus for repairing a blood vessel at a treatment site of a patient. The apparatus includes an elongate hollow prosthesis for placement within a blood vessel. The prosthesis has an inner surface, an outer surface, a first end, and a second end, wherein an electric potential difference may be created between the outer surface and the inner surface.

In another aspect of the invention, there is provided a system for sealing a graft attached within a vessel at a treatment site of a patient, for preventing blood from flowing about the graft. The system includes a balloon catheter. The balloon catheter has an aperture proximate its distal end and includes an inflatable balloon at its distal end. The balloon catheter includes a balloon inflation lumen longitudinally disposed therein and an elongate tubular member lumen longitudinally disposed therein. A leaking site is accessed with a distal end of the balloon catheter by feeding the balloon catheter, via the guide wire lumen, along a guide wire that is disposed longitudinally within a graft attached within a vessel at a treatment site of a patient. The graft extends transversely across a damaged portion of the vessel and thus creates a perigraft space between the graft and the vessel wall. An elongate tubular member is provided having a conductive wire lumen therein and a sharpened distal end.

The sharpened end of the elongate tubular member is advanced through the elongate tubular member lumen such that the sharpened end of the elongate tubular member is proximate the graft. The balloon catheter is inflated via the balloon inflation port, whereby the sharpened end of the elongate tubular member is deflected into a substantially perpendicular relationship with the graft. The elongate tubular member is advanced such that the sharpened end pierces the graft and enters the perigraft space.

A conductive wire is provided. The distal end of the conductive wire is advanced through the proximal end of the elongate tubular member and out of the distal end of the elongate tubular member such that the distal end of the conductive wire enters the perigraft space.

An electric potential source is provided for connection to the conductive wire whereby the conductive wire may be positively electrically charged. A positive electric potential is applied to the conductive wire such that the conductive wire is positively electrically charged. The conductive wire thereby attracts negatively charged blood components within the perigraft space thus forming thrombosis to seal the graft. In another preferred embodiment, a sharpened wire may be used to pierce the graft, thus eliminating the need for an elongate tubular member.

Other features and advantages of the present invention will become more apparent from the following detailed description of the invention when taken in conjunction with the accompanying exemplary drawings.

DETAILED DESCRIPTION OF THE PREFERRED EMBODIMENTS

Figure 1:
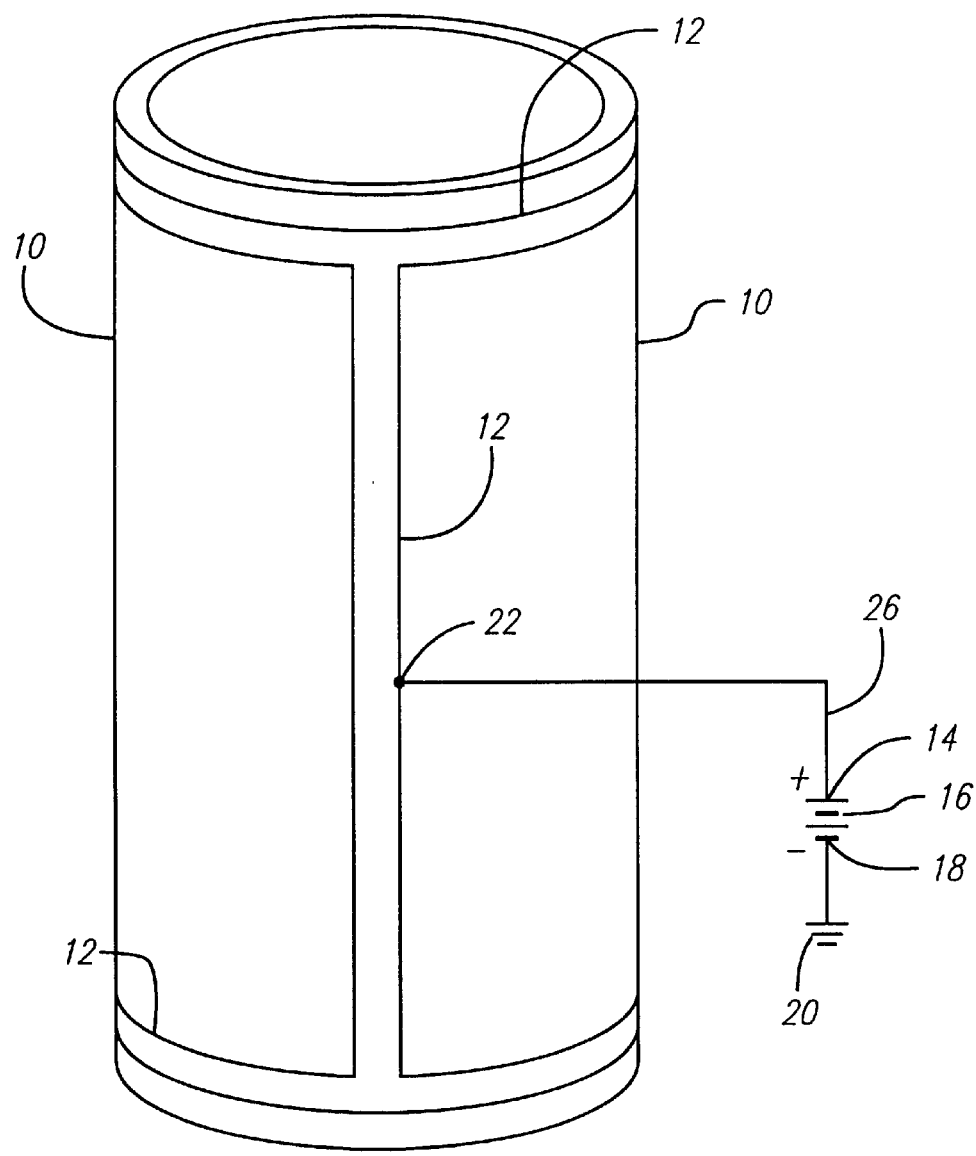
FIG. 1 is an elevational view of a graft having an electrode.

As shown in the exemplary drawings, the present invention is embodied in an apparatus and method for aiding thrombosis through the application of electric potential. Like reference numerals indicate like or corresponding elements among the figures.

As mentioned above, there are various instances where it would be desirable to be able to prevent the rupture of an aneurysm that has been fitted with a leaking graft. It is known that fibrogen, red blood cells, white blood cells, and other protein components of blood are negatively charged. Due to the fact that the blood components are negatively charged, thrombus formation may be induced by the introduction of a positive charge in the blood.

In accordance with the present invention, FIG. 1 depicts a hollow prosthesis such as graft 10 with conductive material 12 applied to the graft and connected to means for supplying a positive electric potential or other electric potential source, such as positive terminal 14 of battery 16. The conductive material can include silver, platinum, or other conductive biocompatible materials. The conductive material can be attached to the graft by ion deposition, as is known in the art, or by other means including mechanical means.

The negative terminal 18 of the battery is connected to ground 20, the ground being the patient's body or another suitable object. A connection 22 between the conductive material and the positive terminal of the battery is preferably detachable.

Figure 2:
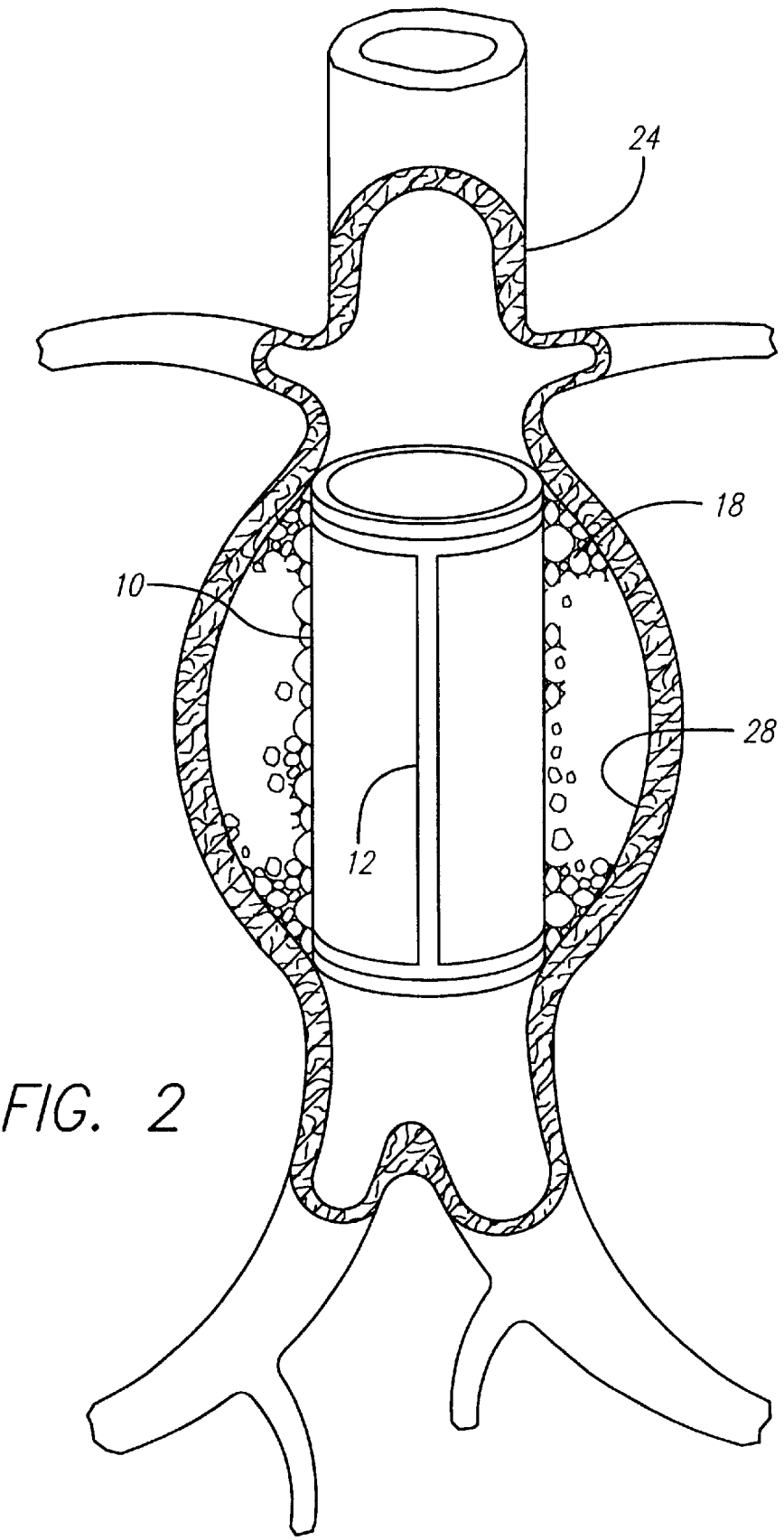
FIG. 2 is an elevational view of the graft of FIG. 1 in use within a blood vessel.

Referring to FIG. 2, graft 10, being connected to battery 16 (FIG. 1) or other suitable device for applying an electric potential, is placed in damaged blood vessel 24 by methods known to those skilled in the art. A lead 26 (FIG. 1) is left connected to conductive material 12 via connection 22. Angiographic fluid is injected into the area. The physician then uses fluoroscopy to determine if perigraft flow is present. If the physician detects perigraft flow, then the conductive material is charged via battery 16. Platelets, being naturally negatively charged, are attracted to the conductive material of such a graft upon placement of the graft within the blood vessel. This causes thrombosis 18 in aneurysm sac 28, thus enhancing the anastomotic seal between the graft and the aneurysm sac. Another angiogram is then performed to ensure that no more perigraft flow is present. Assuming success, the physician then may detach and remove the lead. Alternatively, the physician may again apply a charge to graft 10. Thus, perigraft flow can be repaired in a safe, easy, and efficient manner.

Figure 3:
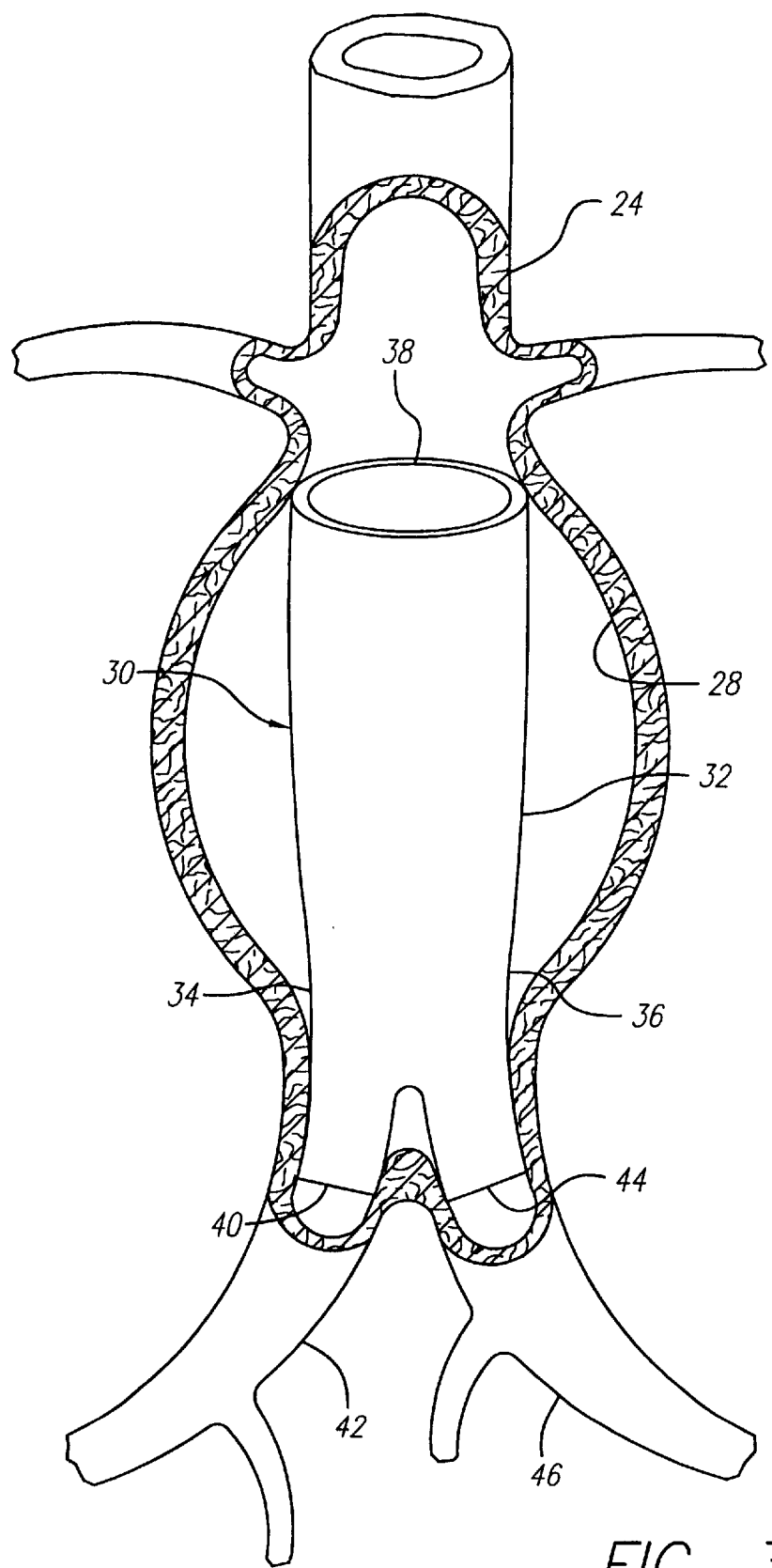
FIG. 3 is an elevational view, with a portion of anatomy shown partially in cross-section, depicting a bifurcated unibody graft for use with the present invention.
Figure 4:
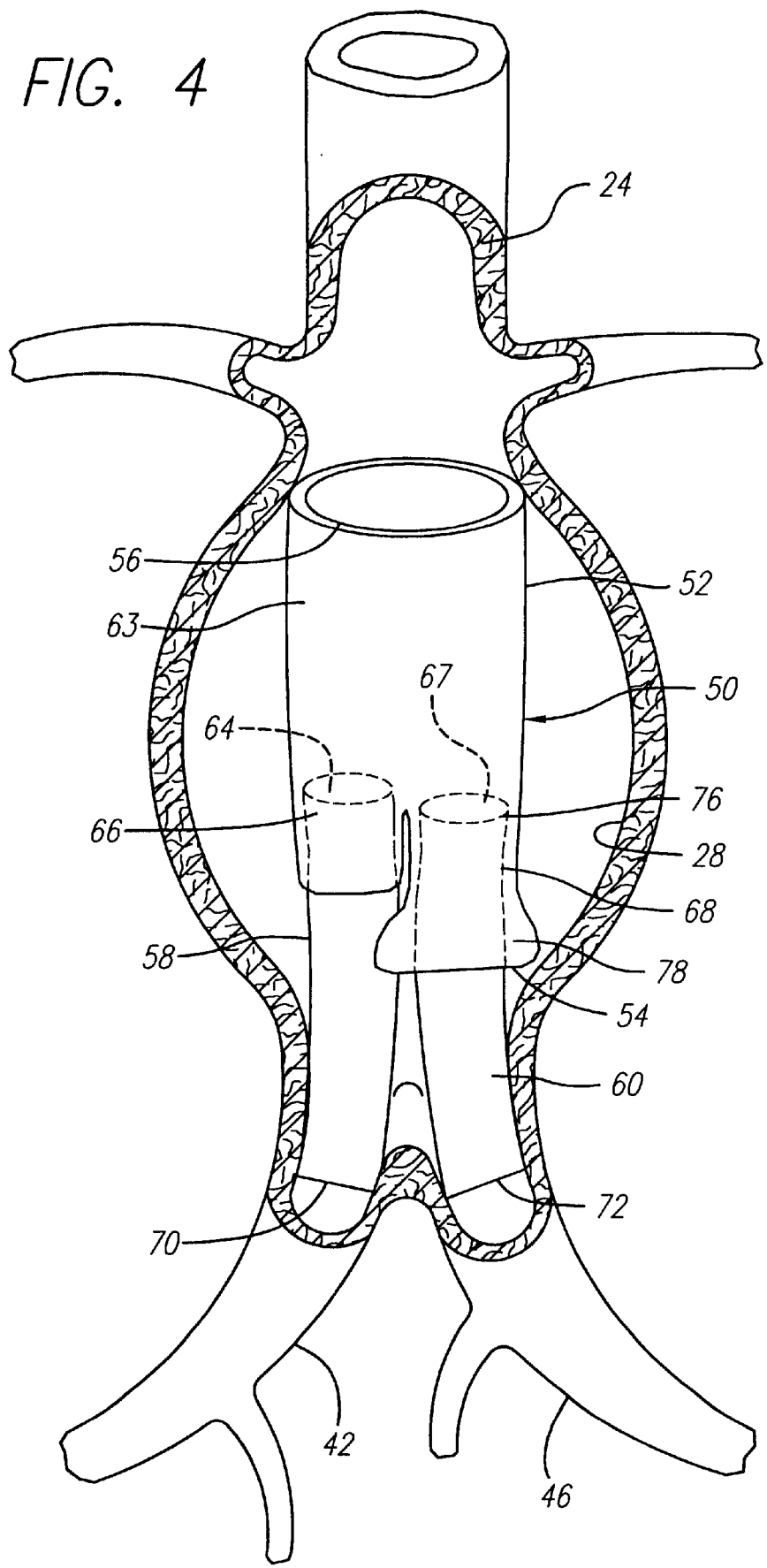
FIG. 4 is an elevational view, with a portion of anatomy shown partially in cross-section, depicting a bifurcated modular graft for use with the present invention.

Turning now to FIGS. 3–4, it is contemplated that the embodiments described herein with respect to tubular grafts may be utilized in conjunction with other types of grafts as well. For example, FIG. 3 depicts bifurcated unibody graft 30. The graft includes trunk 32, first leg 34, and second leg 36. The superior end 38 of the trunk is implanted in a non-dilated portion of a vessel such as abdominal aorta 24. The inferior end 40 of first leg 34 is implanted in an undilated portion of ipsilateral iliac artery 42. The inferior end 44 of second leg 36 is implanted in an undilated portion of contralateral iliac artery 46. The graft 30 can include electrodes as described above. The unibody graft can be used in conjunction with the embodiments of the present invention that utilize grafts.

Referring to FIG. 4, bifurcated modular graft 50 is illustrated as implanted to repair an aneurysm such as abdominal aorta aneurysm 28. The graft 50 includes first graft component 52 having inferior end 54 and superior end 56. The graft 50 also includes second graft component 58, often referred to as the ipsilateral extension, and third graft component 60, often referred to as the contralateral extension. The superior end 56 of trunk 63 is implanted in a non-dilated portion of a vessel such as abdominal aorta 24. The superior end 64 of second graft component 58, or ipsilateral extension, is connected to first graft component 52 at ipsilateral docking site 66. The superior end 67 of third graft component 60, or contralateral extension, is connected to first graft component 52 at contralateral docking site 68. The inferior end 70 of second graft component 58 is implanted in an undilated portion of ipsilateral iliac artery 42. The inferior end 72 of third graft component 60 is implanted in an undilated portion of the contralateral iliac artery 46. The contralateral leg 76 of first graft component 52 terminates in bell-bottom 78. The bell-bottom aids in the surgical implantation and manipulation of the modular graft. The graft 50 can include electrodes as described above. The modular graft can also be used in conjunction with the embodiments of the present invention that utilize grafts.

Figure 5:
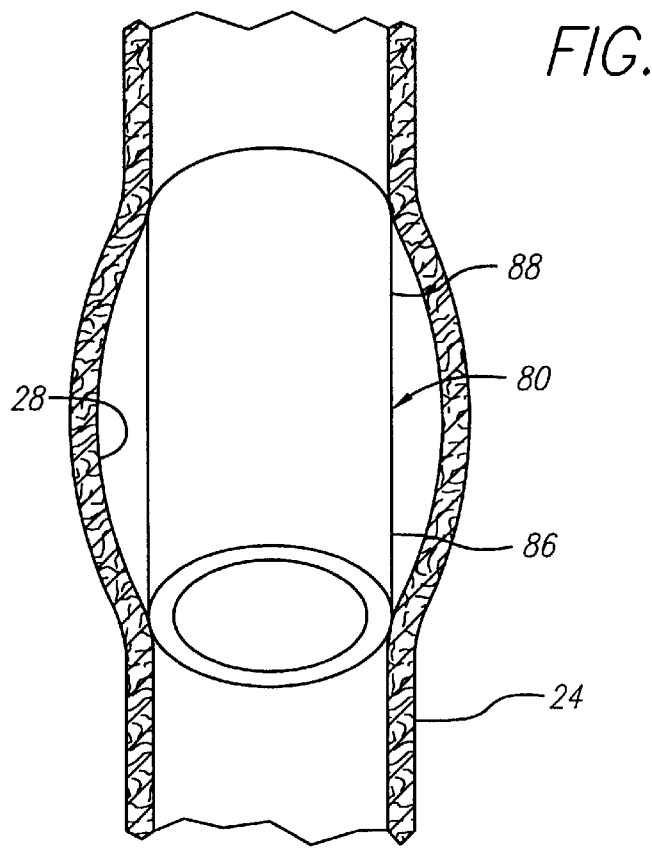
FIG. 5 is a perspective view of an embodiment of the present invention depicting a prosthesis placed within a blood vessel.
Figure 6:
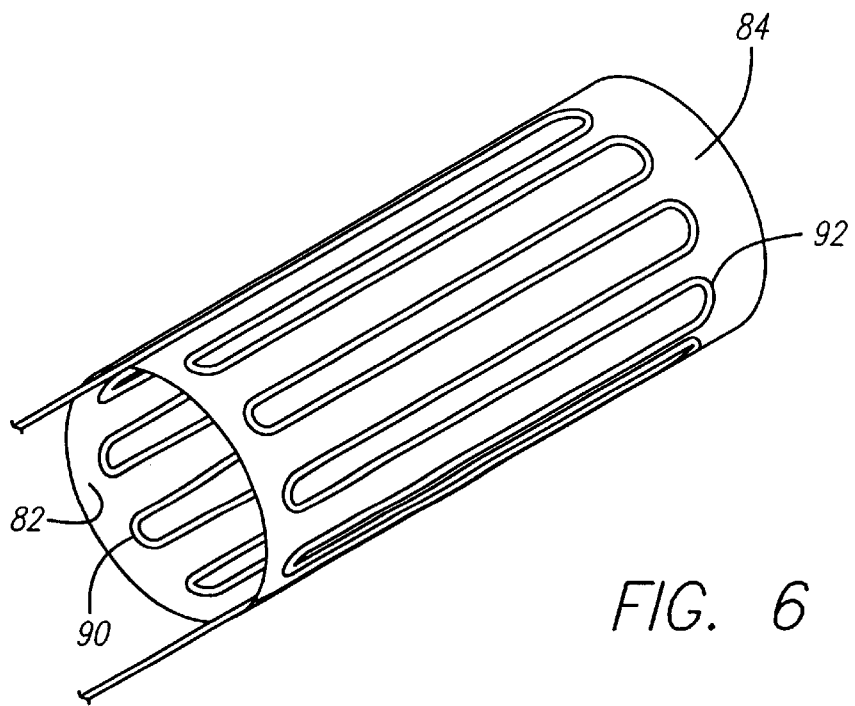
FIG. 6 is a perspective view of the prosthesis of FIG. 5, embodying an electrode on each of its inner and outer surfaces.

Turning now to FIGS. 5 and 6, another presently preferred aspect of the invention for repairing a blood vessel at a treatment site of a patient utilizes elongate substantially cylindrical prosthesis 80. It is contemplated that prosthesis 80 can also assume bifurcated unibody and bifurcated modular configurations, as described above.

The prosthesis 80 is positioned in blood vessel 24 at the treatment site, such as aneurysm sac 28. The prosthesis 80 has inner surface 82, outer surface 84, first end 86, and second end 88. The positioning of prosthesis 80 within blood vessel 24 is done such that the outer surface of each of the ends of the prosthesis comes into apposition with the inner wall of blood vessel 24 to produce a first and second prosthesis-blood vessel interface.

A positive electric potential is applied to outer surface 84 of prosthesis 80 and a negative electric potential is applied to inner surface 82 of prosthesis 80. Consequently, inner surface 82 of prosthesis 80 repels negatively charged blood components and outer surface 84 attracts negatively charged blood components, thereby creating a thrombosis and an anastomotic seal at each of the prosthesis-blood vessel interfaces while allowing for blood to flow freely through the prosthesis. The use of angiograms is also preferable, as described above, to determine is there exists perigraft flow.

Referring to FIG. 6, in one preferred embodiment inner surface 82 is provided with inner electrode 90 and outer surface 84 is provided with outer electrode 92. The inner and outer electrodes may be configured in a serpentine pattern, or any other suitable pattern. The step of applying electric potentials may include applying a positive electric potential to the outer electrode and a negative electric potential to the inner electrode.

It is also contemplated that outer surface 84 can be comprised of an outer material of a first thickness and inner surface 82 can be comprised of an inner material of a second thickness. Outer material and inner material can be chosen such that an electric potential is created between outer surface 84 and inner surface 82 with the outer surface being positively electrically charged and the inner surface being negatively electrically charged. The dimensions of the first thickness and the second thickness may be such that the outer material comes into apposition with the inner material.

It is further envisioned that, rather than designing prosthesis 80 from an outer material and an inner material, only one material is used. An inner coating is applied to inner surface 82 and an outer coating is applied to outer surface 84. The outer coating and inner coating are chosen such that an electric potential is created between the outer surface and the inner surface with the outer surface being positively electrically charged and the inner surface being negatively electrically charged.

Figure 7:
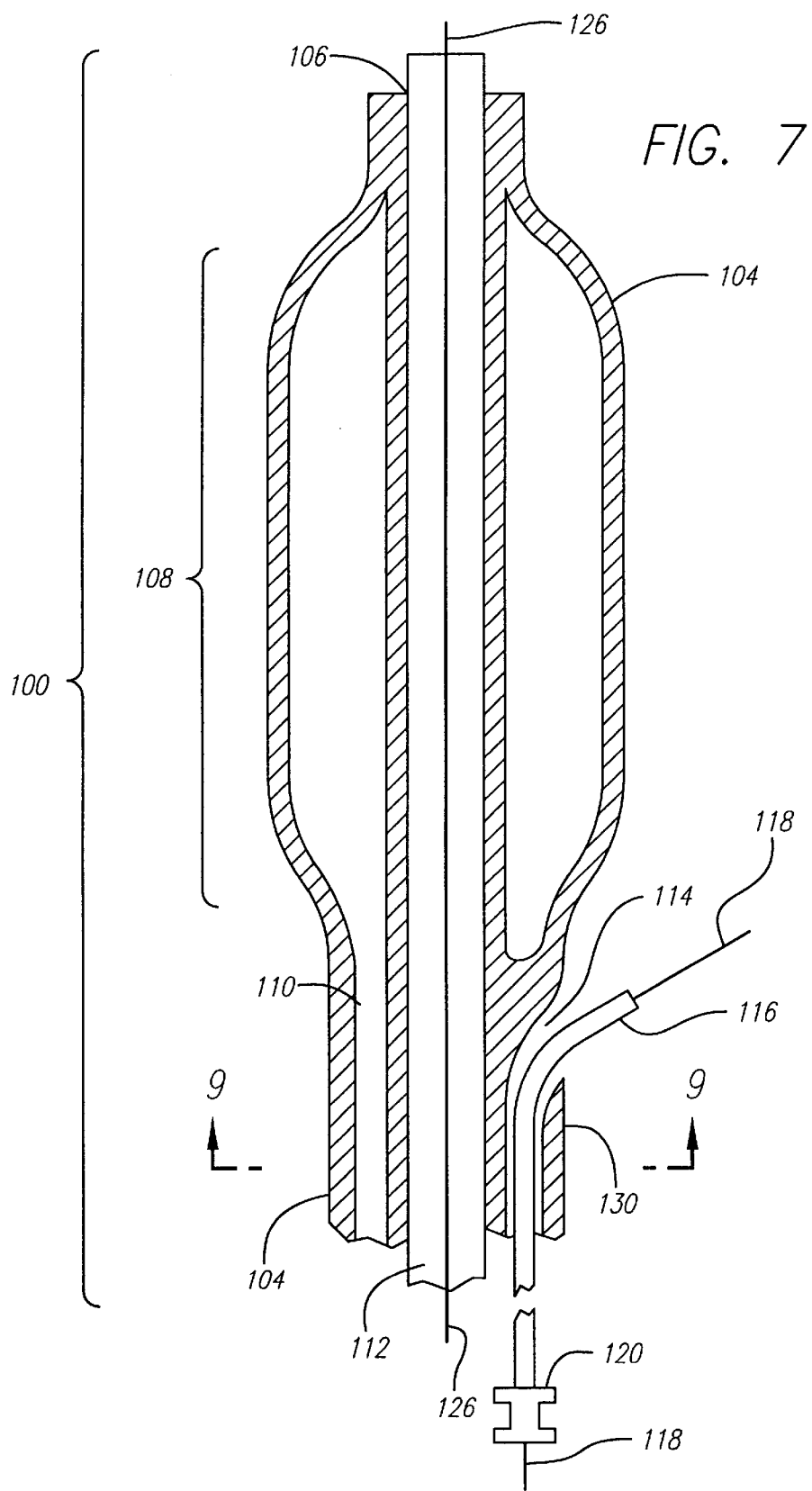
FIG. 7 is an elevational view, partially in section, depicting in detail a balloon catheter of a system for sealing a graft within a vessel, showing the system in assembled relation with the inflatable member of the balloon catheter in an inflated state.
Figure 8:
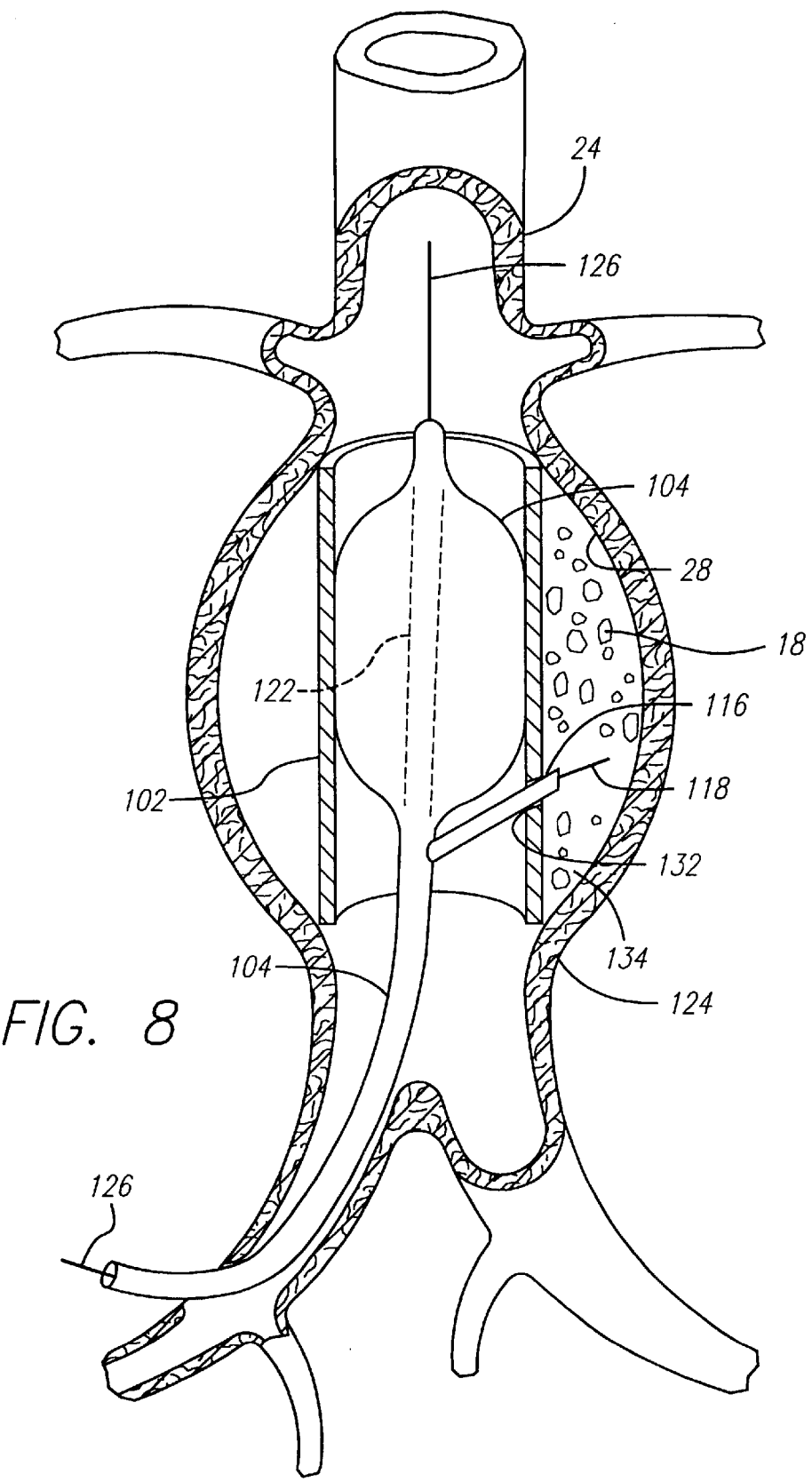
FIG. 8 is an elevational view, partially in section, depicting the system of FIG. 7 in use.
Figure 9:
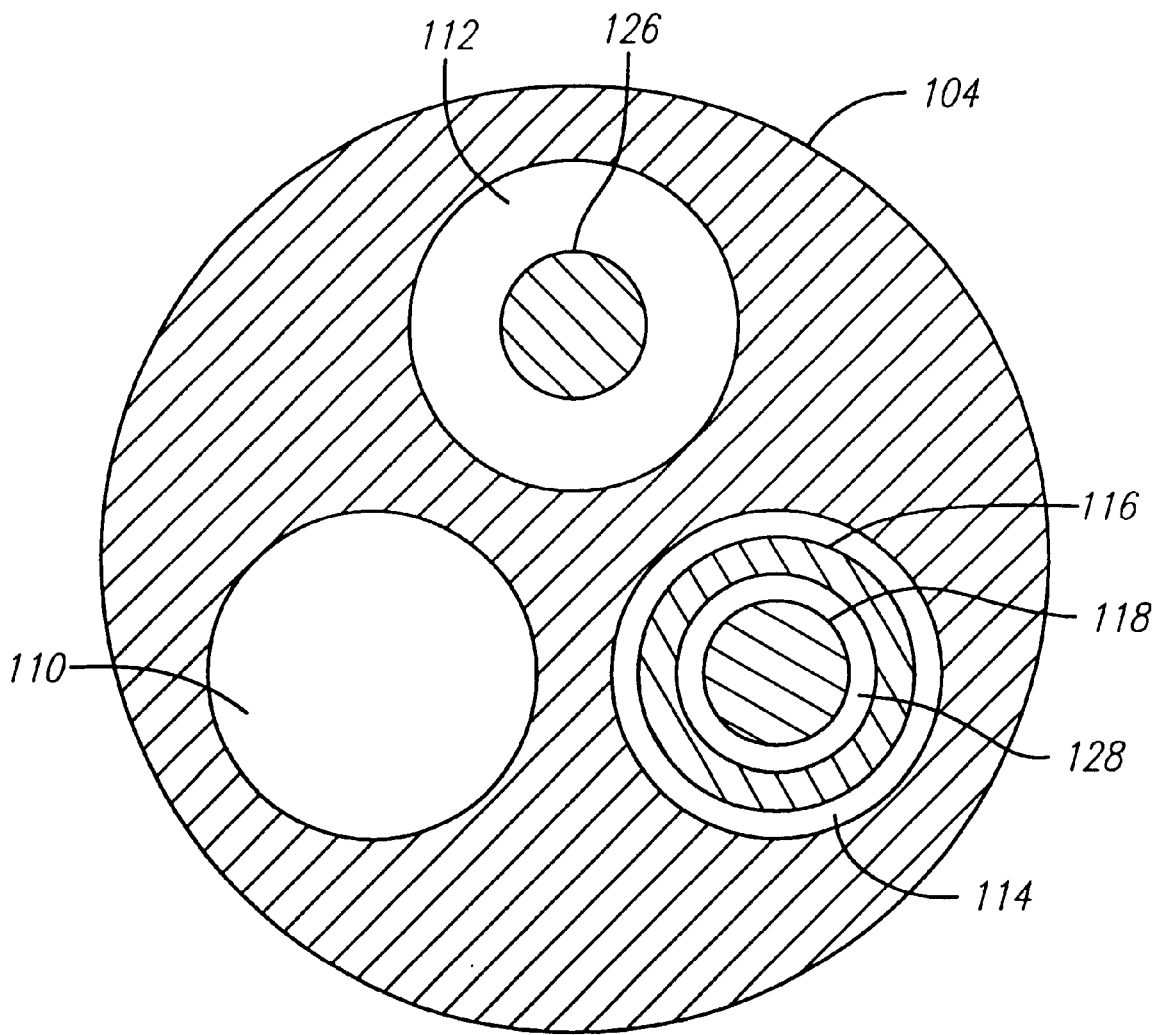
FIG. 9 is a sectional view taken along line 9—9 of FIG. 7.

Turning now to FIGS. 7–9, depicted is system 100 for creating thrombus around graft 102 attached within vessel 24 at a treatment site of a patient, for preventing blood from flowing about the graft. The system includes elongate balloon catheter 104. The balloon catheter has aperture 106 proximate its distal end and includes inflatable balloon 108 at its distal end. Balloon inflation lumen 110, guide wire lumen 112, hypotube lumen 114, or elongate tubular member lumen, and elongate tubular member, or hypotube 116, are longitudinally disposed within balloon catheter 104. The hypotube lumen 114 runs down the proximal end of catheter 104, where the hypotube lumen terminates into an opening. The hypotube 116 preferably has a sharpened distal end and is longitudinally disposed within hypotube lumen 114. The hypotube 116 has a conductive wire lumen. A conductive wire 118 is longitudinally disposed within hypotube 116. Located at the proximal end of hypotube 116 is Luer fitting 120 which is used for facilitating access to the interior of the hypotube. The hypotube 116 is partially disposed within hypotube lumen 114 such that the distal end of the hypotube may protrude from balloon catheter 104. The hypotube 116 may be constructed from any suitable material such as stainless steel or a shape memory alloy. The lumen of the hypotube may be coated or lined with an insulating or non-conductive material to prevent short-circuiting and disrupting an electric potential of the conductive wire.

Referring to FIG. 7, balloon catheter 104 is shown in phantom in deflated state 122 and longitudinally disposed within graft 102. The graft is bridging damaged wall (i.e., an aneurysm sac) 124 of vessel 24.

Referring now to FIG. 8, guide wire 126 is longitudinally disposed within guide wire lumen 112. The guide wire lumen 112 is longitudinally disposed within balloon catheter 104. The conductive wire 118 is longitudinally disposed within conductive wire lumen 128 and extends for the length of hypotube 116. The hypotube 116 is, in turn, longitudinally disposed within hypotube lumen 114 that is protected by support structure 130 (FIG. 7). Thus, the guide wire, guide wire lumen, conductive wire, conductive wire lumen, hypotube, hypotube lumen, and balloon inflation lumen all run substantially parallel to each other within the proximal portion of the balloon catheter.

In one method of the present invention, it is assumed that graft 102, was previously implanted at the treatment site by methods known to those skilled in the art. Angiographic fluid is injected into the area. The physician then uses fluoroscopy to determine if perigraft flow is present. If the physician detects perigraft flow, then conductive wire 118 is inserted into hypotube 116. The hypotube is partially fed through hypotube lumen 114 in deflated balloon catheter 122. The guide wire 126 is advanced through guide wire lumen 112, and using fluoroscopy, to a desired portion of vessel 24 (i.e., through graft 102). Next, deflated balloon catheter 122 is fed along the guide wire until the conductive wire is in the proper position within the graft. The deflated balloon catheter 122 is then inflated via balloon inflation lumen 110. This action angles or deflects hypotube 116 toward wall 132 of the graft or other prosthesis. The hypotube 116 is then advanced distally within the hypotube lumen by hand until the sharpened end of hypotube 116 exits the balloon catheter. The sharpened end of hypotube 116 punctures the wall of the graft and enters perigraft space 134 between the wall of the graft and the wall of vessel 24. The conductive wire 118 is then advanced, via conductive wire lumen 128, until its distal end protrudes from the sharpened end of hypotube 116 and into perigraft space 134 between the wall of the graft and the wall of the vessel. The above-recited steps do not necessarily have to occur in the stated order. For example, hypotube 116 may pierce wall 132 of graft 102 before conductive wire 118 is inserted into the proximal end of the hypotube. Likewise, conductive wire 118 may be inserted into conductive wire lumen 128 after balloon catheter 104 is in place.

A battery having a positive electric terminal and a negative electric terminal, or some other appropriate electric potential source, is provided. A positive electric potential is applied to conductive wire 118 such that the conductive wire is positively electrically charged. The body of the patient or other appropriate object may be used as a ground. Negatively charged blood components are thereby attracted to the conductive wire, thus forming thrombosis 136 that helps effectuate sealing of the graft. Another angiogram is then performed to ensure that no more perigraft flow is present.

In another aspect of the invention, rather than deploying conductive wire 118 through hypotube 116, the conductive wire has a sharpened distal end and is used to pierce wall 132. Thus, the need for a hypotube may be eliminated.

While the invention has been illustrated and described herein in terms of its use as an apparatus and method for aiding thrombosis, it will be apparent to those skilled in the art that the invention can be used in other instances. Other modifications and improvements may be made without departing from the scope of the invention.

What is claimed is:

1. An apparatus for repairing a blood vessel at a treatment site of a patient, comprising:
   an elongate hollow prosthesis for placement within a blood vessel, the prosthesis having an inner surface, an outer surface, a first end, and a second end, wherein an is electric potential difference may be created between the outer surface and the inner surface, the electric potential difference being sufficient to provide thrombosis; and
   an electrode attached to the prosthesis, the electrode having a first circumferentially extending portion spaced from a second circumferentially extending portion connected by a narrow longitudinally extending portion to the first circumferentially extending portion.

2. The apparatus of claim 1, wherein the outer surface has an outer electrode and the inner surface has an inner electrode.

3. The apparatus of claim 2, wherein the outer electrode and the inner electrode are each configured in a serpentine pattern.

4. The apparatus of claim 1, wherein an inner coating is applied to the inner surface and an outer coating is applied to the outer surface, and wherein an electric potential difference is created between the outer surface and the inner surface, the outer surface being positively electrically charged and the inner surface being negatively electrically charged.

5. The apparatus of claim 1, wherein the outer surface of the prosthesis includes a conductive material for use as a positive electrode, the apparatus further including an electric potential source for supplying a positive electric potential to the conductive material, the electric potential source having a positive terminal and a negative terminal, the positive terminal connected to the conductive material, the negative terminal connected to a ground, such that the application of a positive electric potential to the conductive material causes negatively charged components of blood to be attracted to the graft, thus aiding in thrombosis.

6. The apparatus of claim 5, further comprising a detachable connection between the conductive material and the positive terminal of the electric potential source.

7. The apparatus of claim 1, wherein the electric potential difference is provided to seal the apparatus within a blood vessel.

* * * * *

UNITED STATES PATENT AND TRADEMARK OFFICE
CERTIFICATE OF CORRECTION

PATENT NO.  : 6,658,288 B1
DATED       : December 2, 2003
INVENTOR(S) : Reid Hayashi It is certified that error appears in the above-identified patent and that said Letters Patent is hereby corrected as shown below:

<u>Column 6,</u>
Line 28, delete "is" before "electric".

Signed and Sealed this

Ninth Day of March, 2004

JON W. DUDAS
*Acting Director of the United States Patent and Trademark Office*